US007700810B2

(12) United States Patent
Kourtakis et al.

(10) Patent No.: US 7,700,810 B2
(45) Date of Patent: Apr. 20, 2010

(54) CATALYTIC CONVERSION OF ETHANOL TO A 1-BUTANOL-CONTAINING REACTION PRODUCT USING A THERMALLY DECOMPOSED HYDROTALCITE CATALYST

(75) Inventors: Kostantinos Kourtakis, Media, PA (US); Michael B. D'Amore, Wilmington, DE (US); Leo Ernest Manzer, Wilmington, DE (US)

(73) Assignee: E.I. du Pont de Nemours and Company, Wilmington, DE (US)

( * ) Notice: Subject to any disclaimer, the term of this patent is extended or adjusted under 35 U.S.C. 154(b) by 57 days.

(21) Appl. No.: 12/196,485

(22) Filed: Aug. 22, 2008

(65) Prior Publication Data

US 2009/0054705 A1 Feb. 26, 2009

Related U.S. Application Data

(60) Provisional application No. 60/965,712, filed on Aug. 22, 2007.

(51) Int. Cl.
C07C 29/34 (2006.01)
C07C 29/32 (2006.01)
(52) U.S. Cl. .................... 568/902.2; 568/902; 568/905
(58) Field of Classification Search ................ 568/902, 568/902.2, 905
See application file for complete search history.

(56) References Cited

U.S. PATENT DOCUMENTS 5,300,695 A 4/1994 Radlowski

FOREIGN PATENT DOCUMENTS

GB 278141 A 1/1938
WO 2006059729 A1 6/2006

OTHER PUBLICATIONS

International Search Report and Written Opinion, PCT/US2008/074004, (Aug. 22, 2008).
DiCosimo J. I., et al., "Structure and Surface and Catalytic Properties of Mg-Al Basic Oxides" Journal of Catalysis, vol. 178, (Jan. 1, 1998).
Dietz V. K., et al., :"Effect Of The Acid-Base Properties Of Mg-Aimixed Oxides On The Catalyst Deactivation During Aldol Condensation Reactions" Latin American Applied Research, Bahia, Blanca, vol. 33, (Jan. 1, 2003). pp. 79-86 XP008096892 ISSN: 0327-0793.
J. Logsdon, Kirk-Othmer Encyclopedia of Chemical Technology, 2001, John Wiley & Sons (Book Not Included—Available Upon Request).
M. N. Dvornikoff et al., Condensation of Alcohols, J. of Organic Chemistry, 1957, vol. 11:540-542.
J. I. Discosimo et al., Structural Requirements and Reaction Pathways in Condensation Reactions of Alcohols on Mg AlO Catalyts, Journal of Catalysis, 2000, vol. 190:261-275.
J. I. Discosimo et al., Structure and Surface and Catalytic Properties of Mg-Al Basic Oxides, Journal of Catalysis, 1998, vol. 178:499-510.
Carlini et al., Guerbet Condensation of Methanol With N-Propanol to Isobutyl Alcohol Over Heterogeneous Bifunctional Catalysts Based on Mg-Al Mixed Oxides Partially Substituted by Different Metal Componenets, Journal of Molecular Catalysis A: Chemical, 2005, vol. 232:13-20.
C. Carlini et al., Guerbet Condensation of Methanol With N-Propanol to Isobutyl Alcohol Over Heterogeneous Copper Chromite/Mg-Al Mixed Oxides Catalysts, Journal of Molecular Catalysis A: Chemical, 2004, vol. 220:215-220.
V. K. Diez et al., Effect of the Acid-Base Properties of Mg-A11 Mixed Oxides on the Catalyst Deactivation During Aldol Condensation Reactions, Latin American Applied Research, 2003, vol. 33:79-86.
N. N. Das et al., Catalytic Characterization of Bi-Functional Catalysts Derived From Pd-MG-A1 Layered Double Hydroxides, Bull. Mater. Sci., 2002, vol. 25:283-289.
H. S. Fogler, Elements of Chemical Reaction Engineering, 2nd Edition, 1992, (Book Not Included—Available Upon Request).

*Primary Examiner*—Elvis O Price

(57) ABSTRACT

Hydrotalcites are partially or fully thermally decomposed to provide catalysts useful for the conversion of ethanol to a reaction product comprising 1-butanol.

10 Claims, 2 Drawing Sheets

CATALYTIC CONVERSION OF ETHANOL TO A 1-BUTANOL-CONTAINING REACTION PRODUCT USING A THERMALLY DECOMPOSED HYDROTALCITE CATALYST

CROSS-REFERENCE TO RELATED APPLICATIONS

This application claims benefit of priority from Provisional Application No. 60/965,712, filed Aug. 22, 2007. This application relates to commonly-assigned applications filed concurrently on Aug. 22, 2008 as application Ser. Nos. 12/196,518 12/196,540 12/196,578 12/176,602 12/196,651.

FIELD OF THE INVENTION

The present invention relates to the catalytic conversion of ethanol to a 1-butanol-containing reaction product. Various organic chemicals, including 1-butanol itself, can be separated from the reaction product. The catalysts are hydrotalcites, optionally containing transition metals, which have been thermally decomposed, either partially or fully, to form catalytically active species.

BACKGROUND

Efforts directed at improving air quality and increasing energy production from renewable resources have resulted in renewed interest in alternative fuels, such as ethanol and butanol, that might replace gasoline and diesel fuel, or be used as additives in gasoline and diesel fuel.

It is known that 1-butanol can be prepared by condensation from ethanol over basic catalysts at high temperature using the so-called "Guerbet Reaction." See for example, J. Logsdon in Kirk-Othmer Encyclopedia of Chemical Technology, John Wiley and Sons, Inc., New York, 2001.

Methods of using catalysts to convert ethanol to butanol are also discussed in the following references.

M. N. Dvornikoff and M. W. Farrar, J. of Organic Chemistry (1957), 11, 540-542, disclose the use of MgO—$K_2CO_3$—$CuCrO_2$ catalyst system to promote ethanol condensation to higher alcohols, including 1-butanol. The disclosed liquid phase reaction using this catalyst showed a 13% conversion of ethanol and 47% selectivity to 1-butanol.

U.S. Pat. No. 5,300,695, assigned to Amoco Corp., discloses processes in which an alcohol having X carbon atoms is reacted over an L-type zeolite catalyst to produce a higher molecular weight alcohol. In some embodiments, a first alcohol having X carbon atoms is condensed with a second alcohol having Y carbon atoms to produce an alcohol having X+Y carbons. In one specific embodiment, ethanol is used to produce butanol using a potassium L-type zeolite.

J. I. DiCosimo, et al., in Journal of Catalysis (2000), 190 (2), 261-275, describe the effect of composition and surface properties on alcohol-coupling reactions using $Mg_yAlO_x$ catalysts for alcohol reactions, including ethanol. Also condensation reactions on $Mg_yAlO_x$ samples involved the formation of products containing a new C—C bond, such as n-$C_4H_8O$ (or n-$C_4H_9OH$) and iso-$C_4H_8O$ (or iso-$C_4H_9OH$). They also describe, in Journal of Catalysis (1998), 178(2), 499-510, that the oxidation to acetaldehyde and the aldol condensation to n-butanol both involve initial surface ethoxide formation on a Lewis acid-strong base pair.

WO 2006059729 (assigned to Kabushiki Kaisha Sangi) describes a process for efficiently producing, from ethanol as a raw material, higher molecular weight alcohols having an even number of carbon atoms, such as 1-butanol, hexanol and the like. The higher molecular weight alcohols are yielded from ethanol as a starting material with the aid of a calcium phosphate compound, e.g., hydroxyapatite $Ca_{10}(PO_4)_6(OH)_2$, tricalcium phosphate $Ca_3(PO_4)_2$, calcium monohydrogen phosphate $CaHPO_4\times(0-2)H_2O$, calcium diphosphate $Ca_2P_2O_7$, octacalcium phosphate $Ca_8H_2(PO_4)_6\times5H_2O$, tetracalcium phosphate $Ca_4(PO_4)_2O$, or amorphous calcium phosphate $Ca_3(PO_4)_2\times nH_2O$, preferably hydroxyapatite, as a catalyst, the contact time being 0.4 second or longer.

Carlini et al. describe a catalytic reaction of methanol with n-propanol to produce isobutyl alcohol. The involved catalyst is a calcined hydrotalcite in combination with copper chromite. See C. Carlini et al, Journal of Molecular Catalysis A: Chemical (2005), 232 (1-2) 13-20. See also C. Carlini, Journal of Molecular Catalysis A: Chemical (2004), 220 (2), 215-220, in which the catalyst is a mixture of a hydrotalcite with Pd, Ni, Rh, or Cu, with the mixture being calcined at 500° C.

Hydrotalcites are layered, double hydroxides of the general formula

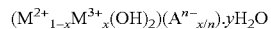

$(M^{2+}_{1-x}M^{3+}_x(OH)_2)(A^{n-}_{x/n}) \cdot yH_2O$

The $M^{2+}$ ions can be a variety of divalent cations (e.g., Mg, Ni, Pt, Pd, Zn, Co, Fe, Cu) and the $M^{3+}$ ions can be trivalent Al, Fe or Cr. Some hydrotalcites are described by V. K. Diez, C. R. Apesteguia, and J. I. DiCosimo (Latin American Applied Research, 33, 79-86 (2003)) and N. N. Das and S. C. Srivastava (Bull. Mater. Sci. 25, (4), 283-289 (2002)).

It has been found that partially or fully thermally decomposed hydrotalcites, particularly those that incorporate transition metals, are catalysts that are effective for the conversion of ethanol to a reaction product that comprises (i.e., contains, among other things) 1-butanol.

SUMMARY OF THE INVENTION

Certain hydrotalcites, as described herein, are partially or fully thermally decomposed to provide catalysts useful for the conversion of ethanol to a 1-butanol-containing reaction product. Various organic chemicals, including 1-butanol itself, or mixtures of organic chemicals, can be separated from the reaction product.

DESCRIPTION

Figure 1:
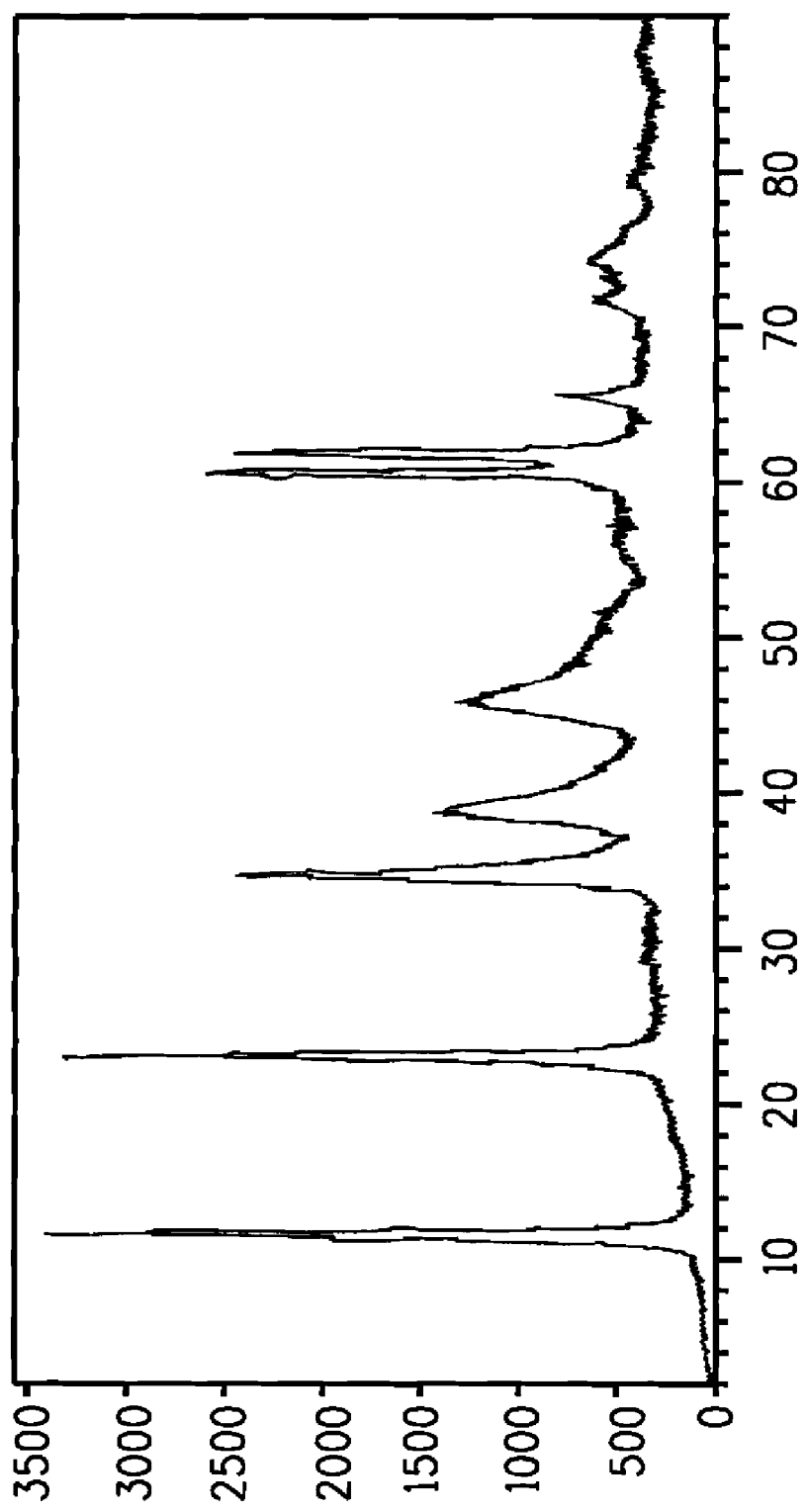
FIG. 1 shows the powder X-ray diffraction pattern of the hydrotalcite material of Example 2 before calcination, and indicates reflections typical of a hydrotalcite phase.
Figure 2:
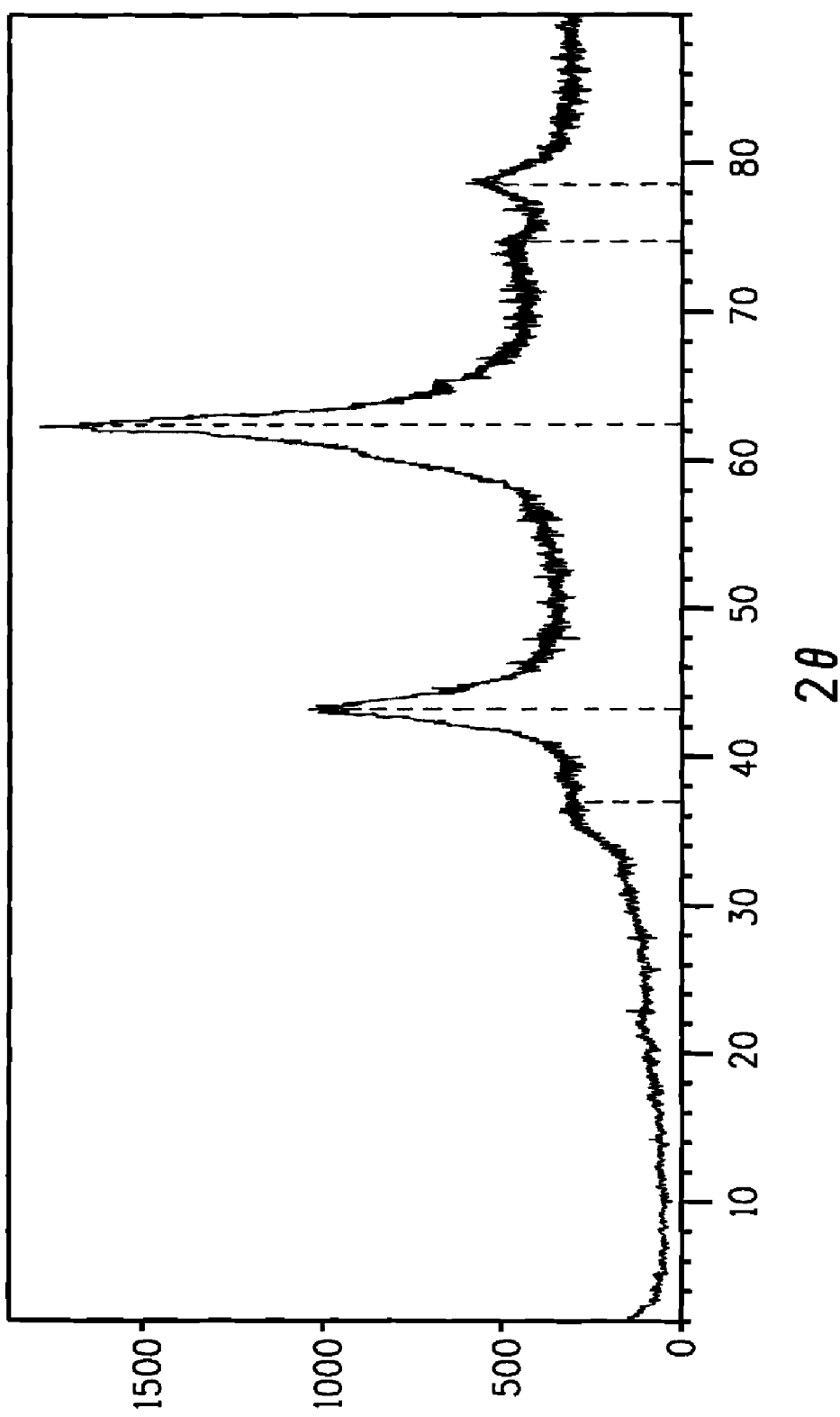
FIG. 2 shows the powder X-ray diffraction pattern of the material of FIG. 1 after calcination, showing decomposition of the hydrotalcite phase by the substantial loss of those reflections that are typical of a hydrotalcite phase.

A stream of gas phase ethanol (that may contain some water, and may be diluted with an inert gas such as nitrogen and carbon dioxide) is contacted with at least one thermally decomposed hydrotalcite catalyst at a temperature and pressure sufficient to produce a reaction product comprising water, unreacted ethanol (if less than complete ethanol conversion), butanol, higher alcohols (higher in the sense that they contain more than 4 carbon atoms) and other organic species. The butanol is predominantly 1-butanol. Suitable temperatures are in the range of about 150° C. to about 500° C., for example about 200° C. to about 500° C. Suitable pressures are from about 0.1 MPa to about 20.7 MPa.

The catalysts that are useful in the present invention are partially or fully thermally decomposed hydrotalcites of the empirical formula (prior to decomposition):

$(M^{2+}_{1-x}M^{3+}_x(OH)_2)(A^{n-}_{x/n}).yH_2O$ wherein $M^{2+}$ is divalent Mg, or a combination of divalent Mg and at least one divalent member selected from the group consisting of Zn, Ni, Pd, Pt, Co, Fe, and Cu;

$M^{3+}$ is trivalent Al, or a combination of trivalent Al and at least one trivalent member selected from the group consisting of Fe and Cr;

x is 0.66 to 0.1;

$A^{n-}$ is $CO_3^{2-}$ with n=2, or $OH^-$ with n=1; and y is 0 to 4.

In a preferred embodiment, in the empirical formula $M^{2+}$ is divalent Mg and at least one divalent member selected from the group consisting of Zn, Ni, Pd, Pt, Co, Fe, and Cu, $M^{3+}$ is trivalent Al, and $A^{n-}$ is $CO_3^{2-}$ (n=2) or $OH^-$ (n=1).

The catalysts that are useful in the present invention are derived from a hydrotalcite of the formula as defined above by a process comprising heating the hydrotalcite for a time and at a temperature sufficient to cause a diminution in the hydrotalcite powder X-ray diffraction pattern peak intensities between 2θ angles of 10 degrees and 70 degrees using CuKα radiation.

GENERAL METHODS

Catalysts derived from the hydrotalcite can be synthesized by the following method. An aqueous salt solution containing (a) divalent magnesium, and, optionally, one or more divalent metals selected from the group consisting of zinc, nickel, palladium, platinum, cobalt, iron, and copper and (b) trivalent aluminum and, optionally, one or more trivalent metals selected from the group consisting of iron and chromium is prepared. Preferred salts are nitrates, chlorides, or acetates. Most preferred are nitrates. The salt solution is added to a basic, aqueous solution containing sodium or potassium carbonate (or bicarbonate), sodium, potassium or ammonium hydroxide, or a mixture of carbonate (or bicarbonate) and hydroxide. (Alternatively, a plurality of individual metal salt solutions may be used, provided that they are added concurrently to the basic, aqueous solution containing the carbonate, bicarbonate, hydroxide or mixtures thereof.) The pH of this basic solution is typically adjusted to a pH of approximately 10 during the addition of the aqueous salt solution. Preferably, the (a) magnesium and optional divalent metals and the (b) aluminum and optional trivalent metals are in a molar ratio (a)/(b) between 0.5/1 and 9/1 inclusive (i.e., including the endpoints 0.5/1 and 9/1 of the range).

The resulting suspension that is formed (i.e., a precipitate suspended in a liquid) can be aged, preferably for approximately 18 hours, at 60° C. to 70° C. The precipitate is then separated, generally by filtering, and subsequently dried (generally in a vacuum oven or in air). The dried precipitate can be analyzed by powder X-ray diffraction to confirm the presence of a hydrotalcite phase. This phase is isostructural with the hydrotalcite $Mg_6Al_2(CO_3)(OH)_{16}.4H_2O$ (JCPDS card # 54-1030; Powder Diffraction Files, International Centre for Diffraction Data, 1601 Park Lane, Swarthmore, Pa. 19081). The dried precipitate is then calcined, to achieve partial decomposition, by heating it for a time and at a temperature sufficient to cause a diminution in the hydrotalcite powder X-ray diffraction pattern peak intensities between 2θ angles of 10 degrees and 70 degrees using CuKα radiation. The calcined material can be analyzed by powder X-ray diffraction to confirm the diminution (including the complete absence) in these peak intensities and the appearance of new peaks corresponding to a material which is isostructural with partially crystalline magnesium oxide (MgO, JCPDS card # 65-0476). Partial decomposition is preferably achieved by calcining the dried precipitate for a time and at a temperature sufficient to substantially reduce the peak intensities characteristic of the hydrotalcite phase.

Although any calcination protocol can be used, one that is particularly useful on a laboratory scale includes heating the hydrotalcite in a one inch (2.5 centimeter [cm]) diameter tube furnace from about 25° C. to 360° C. over 140 minutes at 2.4° C. per minute, and then holding at 360° C. for about 2 to about 4 hours.

The catalysts usable in the process of the invention can be prepared as described above. The catalysts may be used in the form of powders, granules, or other particulate forms. Selection of an optimal average particle size for the catalyst will depend upon such process parameters as reactor residence time and desired reactor flow rates.

The catalytic conversion of ethanol to the reaction product can be run in either batch or continuous mode as described, for example, in H. Scott Fogler, (*Elements of Chemical Reaction Engineering*, $2^{nd}$ Edition, (1992) Prentice-Hall Inc, CA). Suitable reactors include fixed-bed, adiabatic, fluid-bed, transport bed, and moving bed.

It is preferable, but not essential, to treat the catalyst, prior to its use, with nitrogen or air at elevated temperatures, which is thought to remove unwanted carbonates from the catalyst surface. If the starting hydrotalcite contains Ni, Pd, Pt, Co, or Cu, it is also preferred, but not essential, to treat the catalyst, prior to its use, with hydrogen at elevated temperatures. One protocol that has been found to be effective is described in more detail in Example 1, below. If catalyst treatment is desired, the catalyst may be treated in situ in the reactor or ex situ and then introduced into the reactor.

During the course of the reaction, the catalyst may become fouled, and, therefore, it may be necessary to regenerate the catalyst. Preferred methods of catalyst regeneration include, contacting the catalyst with a gas such as, but not limited to, air, steam, hydrogen, nitrogen or combinations thereof, at an elevated temperature, although care must be taken not to use a temperature that is so high that the regeneration results in a loss of surface area or other unwanted effects. If catalyst regeneration is desired, the catalyst may be regenerated in situ in the reactor or ex situ and then introduced into the reactor.

One skilled in the art will know that conditions, such as temperature, catalytic metal, catalyst support, reactor configuration and time can affect the reaction kinetics, product yield and product selectivity. Standard experimentation can be used to optimize the yield of 1-butanol from the reaction.

1-Butanol can be separated from the reaction product by known chemical engineering methods, including distillation. Other specific chemicals (or combinations of chemicals) also can be removed from the reaction product using known chemical engineering methods. The specific methods will be dependent on the nature of the reaction product, which, in turn, is dependent on the specific catalyst used and the reaction conditions, particularly the extent of ethanol conversion.

Although particular embodiments of the present invention have been described in the foregoing description, it will be understood by those skilled in the art that the invention is

EXAMPLES

Example 1

$(M^{2+}_{1-x}M^{3+}_{x}(OH)_2)(A^{n-}_{x/n}) \cdot yH_2O$ Hydrotalcite of Formula $M^{2+}=Mg^{2+}$; $M^{3+}=Al^{3+}$; $A^{n-}=CO_3^{2-}$; n=2; x=0.25; and y=0.5

5.5 g of $NaHCO_3$ was dissolved in 250 milliliters (ml) of water in a three neck, round bottom flask and heated to 65° C. The pH was adjusted to approximately 10 by adding 2 M NaOH solution. 18.8 g of aluminum nitrate $(Al(NO_3)_3 \cdot 9H_2O$ (EMD Sciences, Gibbstown, N.J.) was dissolved in 100 ml of water, and 38.4 g of magnesium nitrate $(Mg(NO_3)_2 \cdot 6H_2O$ (EMD Sciences, Gibbstown, N.J.) was dissolved in 100 ml of water. These latter two solutions were added concurrently and drop-wise to the preheated solution containing the sodium bicarbonate/sodium hydroxide mixture. After complete addition of the metal nitrate solutions, the suspension was kept at 65° C. (with stirring) for 1 hour (hr) and then left for aging at the same temperature for 18 hrs without stirring.

The resulting precipitate was separated from solution by filtering. The precipitate was dried in a vacuum oven at 90° C. for 48 hrs and calcined in nitrogen for 2 hours at 360° C. The heating protocol was as follows: The precipitate was placed in a 1 inch (2.5 cm) diameter tube furnace, and the temperature was increased from 25° C. to 360° C. at 2.4° C. per minute over the course of 140 minutes, followed by 360° C. for 2 hours.

Reactor Evaluation

Approximately 2 cubic centimeters (cc) of catalyst was loaded on a stainless steel mesh support within an 18"×½" (45.7 cm×1.3 cm) outside diameter (o.d.) type 360 stainless steel tube reactor with inlets for gas and liquid feeds. The catalyst was pre-conditioned in situ by flowing nitrogen gas through it at a flow rate of 15 cc/min, initially at room temperature, after which the reactor temperature was raised to 350° C., held there for one hour, and then lowered to 300° C. While maintaining the nitrogen flow, ethanol was introduced at a flow rate of 1.03 ml/hr to obtain reaction data at 300° C. (The reactor temperature was subsequently raised to 350 and then 400° C. to obtain reaction data at these two higher temperatures.) (If the catalyst had contained Ni, Pd, Pt, Co or Cu, the pre-conditioning would involve flowing nitrogen gas, initially at room temperature, raising the temperature to 350° C., holding it there for one hour, lowering the temperature to 180° C., flowing hydrogen gas at 15 cc/min for one hour, reintroducing nitrogen gas at a flow rate of 15 cc/min, and increasing the reactor temperature to 300° C. to introduce the ethanol to generate reaction data.) After 60 minutes, reaction off-gases were condensed over a five minute period into cold N-methylpyrrolidone, and the resultant solution was analyzed using an Agilent™ 5890 GC (Palo Alto, Calif.) equipped with flame ionization and mass selective detectors. Results are shown in Table 1, wherein "EtOH" means ethanol, "BuOH" means 1-butanol, "Conv." means conversion, and "Sel." means selectivity. Ethanol conversion (%) was calculated as follows: [(1−carbon moles of unreacted ethanol)/carbon moles of total outlet gases] times 100. Selectivity (%) was calculated as follows: (carbon moles of product/carbon moles of ethanol reacted) times 100.

TABLE 1

| Temp. ° C. | Minutes | EtOH Conv. | BuOH Sel. | BuOH Yield |
|---|---|---|---|---|
| 300 | 60 | 38.9 | 3.1 | 1.2 |
| 350 | 60 | 47.1 | 2.4 | 1.1 |
| 400 | 60 | 46.1 | 3.7 | 1.7 |

Example 2

$(M^{2+}_{1-x}M^{3+}_{x}(OH)_2)(A^{n-}_{x/n}) \cdot yH_2O$ Hydrotalcite of Formula $M^{2+}=Mg^{2+}$; $M^{3+}=Al^{3+}$; $A^{n-}=OH^-$; n=1; x=0.247; and y=0.5

125 ml of water was added to a three neck, round bottom flask and heated to 65° C. The pH was adjusted to about 10 by adding 2 M NaOH solution (NaOH, J T Baker). 13.8 g of aluminum nitrate $(Al(NO_3)_3 \cdot 9H_2O$ (EMD Sciences AX0705-11)) was dissolved in 50 ml of water, and 28.8 g of magnesium nitrate $(Mg(NO_3)_2 \cdot 6H_2O$ (Fluka)) was dissolved in 50 ml of water. These latter two solutions were added concurrently and drop-wise to the preheated NaOH solution. After complete addition of the metal nitrate solutions, the resulting suspension was kept at 65° C. with stirring for 1 hr and then aged at this temperature for 18 hours without stirring.

The precipitate was separated from solution by filtering and washed, twice, with about 250 ml of deionized water. The synthesized, separated solids were dried in vacuum oven at 90° C. for 24 hrs and calcined at 360° C. for 2 hours in nitrogen. The heating protocol was as follows: The precipitate was placed in a 1 inch (2.5 cm) diameter tube furnace, and the temperature was increased from 25° C. to 360° C. at 2.4° C. per minute over the course of 140 minutes, followed by 360° C. for 2 hours.

The catalyst was evaluated as described in Example 1, above, and the results are shown in Table 2.

TABLE 2

| Temp. ° C. | Minutes | EtOH Conv. | BuOH Sel. | BuOH Yield |
|---|---|---|---|---|
| 300 | 60 | 44.1 | 44.6 | 19.7 |
| 350 | 60 | 45.9 | 40.2 | 18.4 |
| 400 | 60 | 71.8 | 22.6 | 16.2 |

What is claimed is:

1. A process for making a 1-butanol-containing product, said process comprising:
   contacting a reactant comprising ethanol with a catalyst at a reaction temperature and pressure sufficient to produce said product, wherein said catalyst is derived from a hydrotalcite of the formula:

$(M^{2+}_{1-x}M^{3+}_{x}(OH)_2)(A^{n-}_{x/n}) \cdot yH_2O$ wherein
   $M^{2+}$ is divalent Mg, or a combination of divalent Mg and at least one divalent member selected from the group consisting of Zn, Ni, Pd, Pt, Co, Fe, and Cu;
   $M^{3+}$ is trivalent Al, or a combination of trivalent Al and at least one trivalent member selected from the group consisting of Fe and Cr;
   x is 0.66 to 0.1;
   $A^{n-}$ is $CO_3^{2-}$ with n=2 or $OH^-$ with n=1; and
   y is 0 to 4;
   wherein the hydrotalcite catalyst is partially decomposed.

2. The process of claim 1, wherein the decomposition is achieved by heating for a time and at a temperature sufficient to cause a diminution in the hydrotalcite powder X-ray diffraction pattern peak intensities between 2θ angles of 10 degrees and 70 degrees using CuKα radiation.

3. The process of claim 1, wherein $M^{2+}$ is divalent Mg.

4. The process of claim 1, wherein $M^{3+}$ is trivalent Al.

5. The process of claim 1, wherein $A^{n-}$ is $CO_3^{2-}$.

6. The process of claim 1, wherein $A^{n-}$ is $OH^-$.

7. The process of claim 1, wherein $M^{2+}$ is $Mg^{2+}$; $M^{3+}$ is $Al^{3+}$; $A^{n-}$ is $OH^-$; n is 1; x is 0.247; and y is 0.5.

8. The process of claim 1, wherein $M^{2+}$ is $Mg^{2+}$; $M^{3+}$ is $Al^{3+}$; $A^{n-}$ is $CO_3^{2-}$; n is 2; x is 0.25; and y is 0.5.

9. The process of claim 1, wherein said reaction temperature is from about 200° C. to about 500° C., and said pressure is from about 0.1 MPa to about 20.7 MPa.

10. The process for making the 1-butanol-containing product of claim 1, said process comprising:
  contacting a reactant comprising ethanol with a catalyst at a reaction temperature and pressure sufficient to produce said product, wherein said catalyst is made by a method comprising:
  a) dissolving a soluble (i) sodium or potassium carbonate or sodium or potassium bicarbonate, or (ii) sodium, potassium or ammonium hydroxide, or (iii) a mixture of (i) and (ii), in water to form a first solution and heating the first solution to between 60° C. and 70° C.;
  b) adjusting the pH of the first solution with hydroxide to a pH of approximately 10;
  c) adding to the first solution (i) at least one magnesium salt and optionally salts of one or more divalent metals selected from the group consisting of Zn, Ni, Pd, Pt, Co, Fe, and Cu; and (ii) at least one aluminum salt and optionally salts of one or more trivalent metals selected from Fe or Cr, wherein (a) said salts are in one or more aqueous solutions, and (b) the magnesium and optional divalent metals of (i) and the aluminum and optional trivalent metals of (ii) are in a molar ratio between 0.5/1 and 9/1 inclusive, thereby forming a suspension whose pH is maintained at approximately 10;
  d) optionally stirring the suspension and maintaining the suspension at a temperature between 60° C. and 70° C.;
  e) aging the suspension of step (c) or step (d) to form a precipitate and separating the precipitate from the suspension; and
  f) partially decomposing the precipitate by heating it for a time and at a temperature sufficient to cause a diminution in hydrotalcite powder X-ray diffraction pattern peak intensities between 2θ angles of 10 degrees and 70 degrees using CuKα radiation, thereby forming said catalyst.

* * * * *